United States Patent [19]

Ayer et al.

[11] Patent Number: 5,126,142

[45] Date of Patent: Jun. 30, 1992

[54] DISPENSER COMPRISING IONOPHORE

[75] Inventors: Atul D. Ayer; Terry L. Burkoth; Anthony L. Kuczynski, all of Palo Alto; Joseph C. Deters, Los Altos, all of Calif.

[73] Assignee: ALZA Corporation, Palo Alto, Calif.

[21] Appl. No.: 641,023

[22] Filed: Jan. 11, 1991

Related U.S. Application Data

[63] Continuation-in-part of Ser. No. 381,423, Jul. 18, 1989.

[51] Int. Cl.⁵ .............................................. A23K 1/18
[52] U.S. Cl. .................................. 424/438; 424/473; 424/422
[58] Field of Search ................. 424/438, 473, 422

[56] References Cited

U.S. PATENT DOCUMENTS

| | | | |
|---|---|---|---|
| 3,133,132 | 5/1965 | Loeb et al. | 264/49 |
| 3,173,876 | 8/1965 | Zobrist | 252/137 |
| 3,276,586 | 10/1966 | Rosaen | 210/90 |
| 3,541,005 | 11/1970 | Strathmann et al. | 210/19 |
| 3,541,006 | 11/1970 | Bixler et al. | 210/23 |
| 3,546,142 | 12/1970 | Michaels et al. | 260/2.1 |
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 4,002,173 | 1/1977 | Manning et al. | 128/296 |
| 4,160,020 | 7/1979 | Ayer et al. | 424/15 |
| 4,207,893 | 6/1980 | Michaels | 128/260 |
| 4,327,725 | 5/1982 | Cortose et al. | 421/473 |
| 4,594,483 | 6/1986 | Eckenhoff et al. | 424/15 |
| 4,783,337 | 11/1988 | Wong et al. | 424/468 |
| 4,814,181 | 3/1989 | Jordan et al. | 424/472 X |
| 4,871,544 | 10/1989 | Eckenhoff | 424/438 |

OTHER PUBLICATIONS

Ann. N. Y. Acad. Sci. vol. 264, pp. 273-286 (1975).
Feedstuff, pp. 14, 15 and 22 (1989).
Kirk-Othmer Encyclopedia, vol. 3, pp. 47-64, (1978).

Primary Examiner—Thurman K. Page
Assistant Examiner—Leon R. Horne
Attorney, Agent, or Firm—Jacqueline S. Larson; Edward L. Mandell; Paul L. Sabatine

[57] ABSTRACT

A dispenser is disclosed for delivering a beneficial ionophore to an animal. The dispenser comprises (1) a semipermeable housing defining an internal space, (2) at least one composition comprising an ionophore and a pharmaceutically acceptable carrier in the space, (3) an expandable hydrophilic composition in the space, (4) a dense member in the space, and (5) at least one exit passageway in the housing for delivering the ionophore from the dispenser.

22 Claims, 5 Drawing Sheets

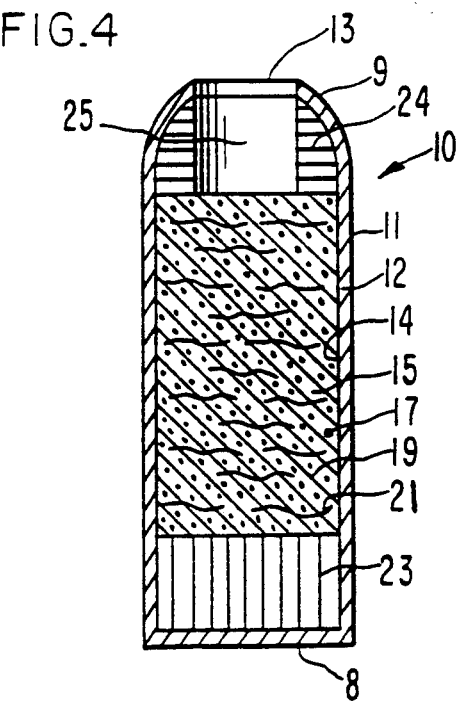
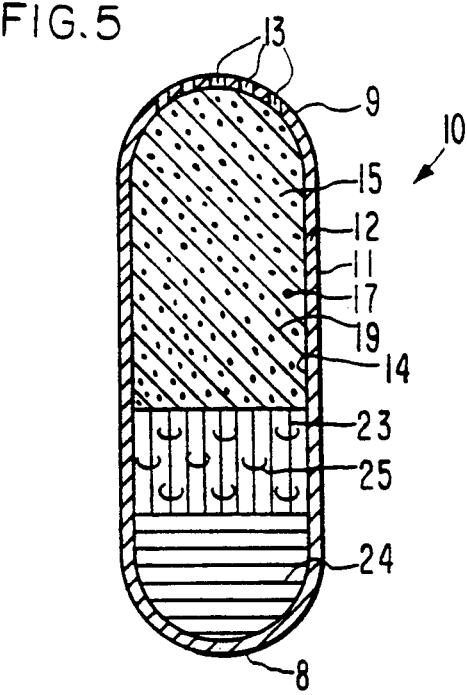
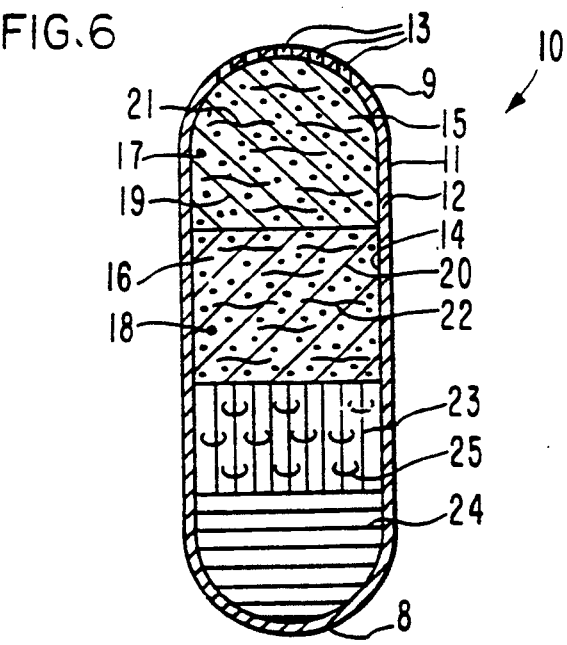
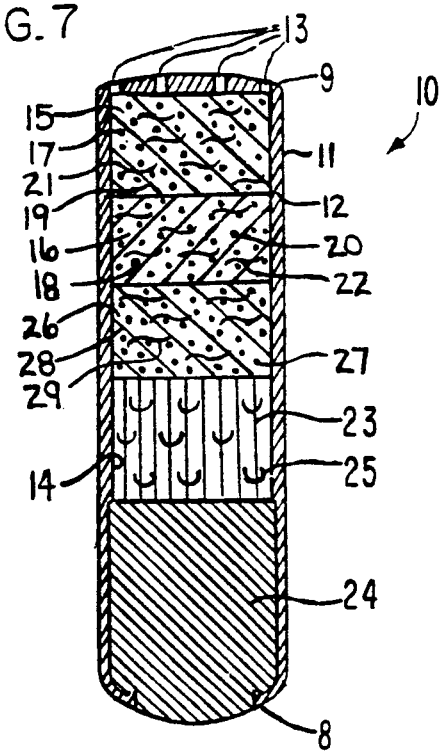

DISPENSER COMPRISING IONOPHORE

This application is a continuation-in-part of application Ser. No. 07/381,423, filed on Jul. 18, 1989.

DESCRIPTION OF TECHNICAL FIELD

This invention pertains to the delivery of an ionophore to an animal, and particularly to livestock. More particularly, the invention is concerned with the controlled administration of an ionophore to an animal for treating an infectious disease, for improving feed efficiency, and for the enhancement of growth of the animal.

DESCRIPTION OF BACKGROUND OF THE INVENTION

Ionophores, or ion-bearers, as reported in Ann. N.Y. Acad. Scil, Vol. 264, pp. 373-86 (1985), are polyether antibiotics that modulate the physiological transport of ions across biological membranes and alter the characteristics of fermentation in the animal, resulting in favorable metabolic changes. These valuable properties of ionophores led to their use as feed additives by the livestock industry. For example, the ionophores, when fed to ruminants, resulted in an improved feed-gain ratio, as reported in Feedstuffs, pp. 14, 15 and 22 (1989). In one accepted use, ionophores are fed to feedlot cattle in confinement for improved feed efficiency. In this use, the ionophore first is mixed with a finely ground nonmedicated feedstuff to produce a premix, which premix is added to an air-dry feed for feeding to cattle, including steers and heifers.

While the above described prior art use of ionophore results in improved feed efficiency, usually of from 5 to 8 percent or higher, for steers and heifers, as reported in Feedstuffs (supra), serious shortcomings accompany this use. For example, since the ionophore is mixed with feed, one shortcoming is the difficulty to ascertain the amount of ionophore ingested by the animal because of feedlot losses such as spillage and scatter. Another shortcoming resides in the absence of controlled administration of known amounts of the ionophore over time, as the composition of the feed charged with the ionophore can vary with feed millers. Also, ionophores are sensitive to moisture in the environment, which moisture can adversely affect their usefulness, and the handling and transport of feeds containing ionophores can result in the segregation of particles carrying ionophores and change the concentration level to which cattle are exposed when fed over time. Then, since ionophores usually are mixed with feeds daily, this requires extra labor that adds to the cost of the ionophore-feedstuff.

In the light of the above presentation, it will be appreciated by those versed in the dispensing art to which this invention pertains that a pressing need exists for a dosage form that can deliver a valuable ionophore to a biological environment of use comprising livestock for both improved feed efficiency and the enhancement of growth of the livestock. The pressing need exists also for a dosage form that can store and deliver an ionophore at a controlled rate in a substantially constant dose per unit time over a prolonged period of time essentially independent of the environment of use, which environment of use pertains to livestock that are confined and to livestock in the pasture. It will be appreciated further by those versed in the dispensing art that if such a novel and unique dosage form is provided that can administer an ionophore in a rate-controlled dose over time and, simultaneously, provide the beneficial effects, the dosage form would represent an advancement and valuable contribution in the ionophore dosage form art.

SUMMARY OF THE INVENTION

The present invention provides a dispenser or other dosage form for delivering an ionophore in a rate-controlled manner to an animal over an extended period of time to produce the desired beneficial ionophore effects. The dispenser comprises a housing defining an internal space or lumen, at least one composition comprising an ionophore and a pharmaceutically acceptable carrier in the space or lumen, an expandable hydrophilic composition in the space or lumen, a densifier in the space or lumen, and at least one exit passageway in the housing for delivering the ionophore from the dispenser. The dispenser can have a high ionophore loading and is self-contained, self-starting and self-powered in a fluid environment of use. The invention also provides a composition of matter comprising an ionophore and a pharmaceutically acceptable carrier for administration to animals.

With the dispenser and the composition of this invention, the ionophore may be dispensed to livestock in the pasture as well as to livestock in confinement. The ionophore may be administered in a different, often lower, overall dosage than the dose required if mixed with foodstuffs, and the amount of ionophore administered is exactly known and can be controlled.

BRIEF DISCLOSURE OF THE DRAWINGS

In the drawing figures, which are not drawn to scale but are set forth to illustrate various embodiments of the invention, the drawing figures are as follows:

FIG. 4 is an opened view of the dosage form of FIG. 2 through 5—5 thereof for illustrating a different structural embodiment of the dosage form;

FIG. 5 is an opened view of the dosage form of FIG. 1, wherein the dosage form depicted in FIG. 5 comprises a different internal arrangement and exit means for delivering an ionophore from the dosage form;

FIG. 6 is an opened view of the dosage form of FIG. 1, wherein the dosage form in FIG. 6 illustrates another embodiment of the internal members and the exit means;

FIG. 7 is an opened view of a dosage form of the invention, illustrating a different structural embodiment and a different internal arrangement of the dosage form.

In the drawing figures and in the specification, like parts in related figures are identified by like reference numerals. The terms appearing earlier in the specification and in the description of the drawing figures, as well as embodiments thereof, are further detailed elsewhere in the disclosure.

DETAILED DISCLOSURE OF THE INVENTION DRAWINGS

Figure 1:
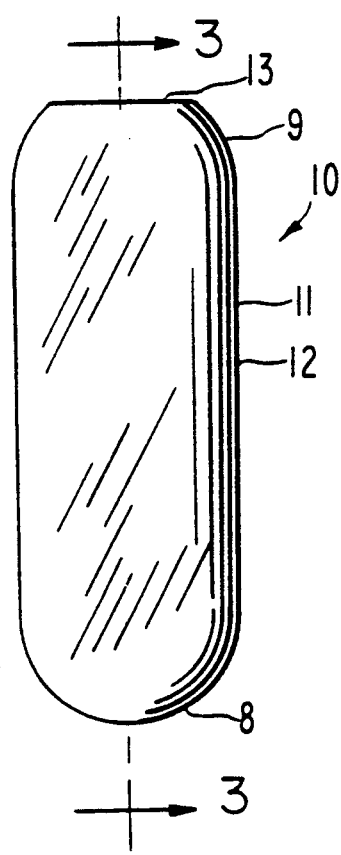
FIG. 1 is a view of a dosage form designed and manufactured as a dispenser for administering a beneficial ionophore to a warm-blooded animal.

Turning now to the drawings in detail, which drawings are examples of various dosage forms provided by the invention and which examples are not to be construed as limiting, one example of a dosage form is seen in FIG. 1. In FIG. 1, a dosage form 10 is seen comprising a body member 11 comprising a wall 12 that surrounds an internal lumen not seen in FIG. 1. Dosage form 10 comprises a lead end 9 and a rear end 8. Lead end 9 comprises a wide exit passageway 13 for releasing a beneficial ionophore form dosage form 10 to a biological environment of use.

Figure 2:
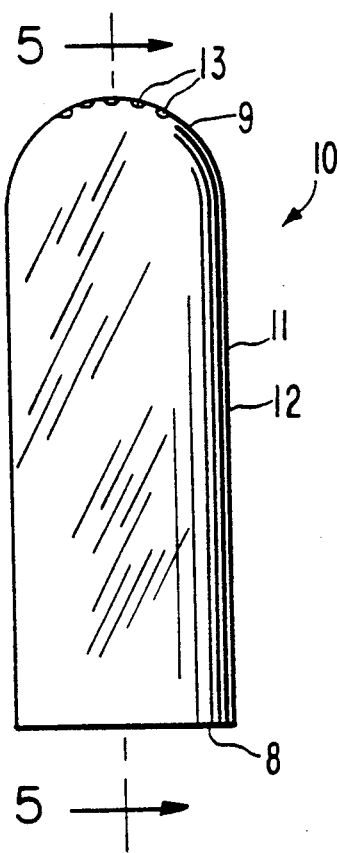
FIG. 2 is a view of another dosage form provided by the invention sized and adapted for administering a beneficial ionophore to a warm-blooded animal over a prolonged period of time.

FIG. 2 illustrates another embodiment of dosage form 10 provided by this invention. In FIG. 2, dosage form 10 comprises lead end 9, rear end 8, body 11 and wall 12. Lead end 9 comprises more than one, or a multiplicity of exit passageways 13 through wall 12 for releasing a beneficial ionophore from dosage form 10.

Figure 3:
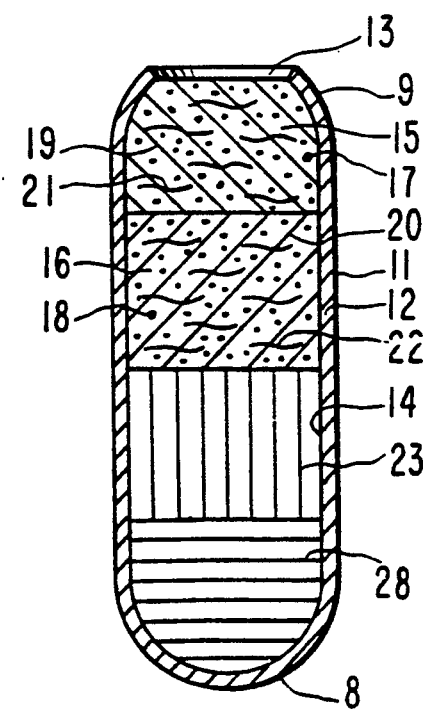
FIG. 3 is an opened view of the dosage form of FIG. 1 through 3—3 thereof for illustrating the structure of the dosage form in one embodiment.

In FIG. 3, dosage form 10 of FIG. 1 is seen in opened section through 3—3 of FIG. 1. In FIG. 3, dosage form 10 comprises lead end 9, rear end 8, a body 11, and a wall 12 that surrounds and forms an internal lumen or compartment 14 that communicates through a wide exit passageway 13 with the exterior of dosage form 10. Wall 12 of dosage form 10 comprises totally a semipermeable composition, or wall 12 comprises at least in part a semipermeable composition. The remainder of wall 12, in the latter embodiment, may comprise a composition that is substantially nonpermeable to the passage of an exterior fluid present in the environment of use. Both semipermeable and nonpermeable portions of wall 12 are substantially impermeable to the passage of ingredients present inside dosage from 10, are non-toxic and maintain physical and chemical integrity during the delivery of the beneficial ionophore from dosage form 10.

Internal compartment or lumen 14 comprises a first composition 15 and a second composition 16. The first composition 15 comprises a beneficial ionophore represented by dots 17, and the second composition 16 comprises a beneficial ionophore represented by dots 18. The first and second compositions comprise at least one or more than one ionophore. The first and second compositions comprise like or unlike ionophores. The first and second compositions comprise the same dosage unit amounts or the compositions comprise different dosage unit amounts of an ionophore. First composition 15 also comprises a pharmaceutically acceptable carrier, represented by slanted lines 19, for ionophore 17; and the second composition 16 also comprises a pharmaceutically acceptable carrier, represented by slanted lines 20, for ionophore 18. Carriers 19 and 20 can be the same or different in compositions 15 and 16. In both embodiments carriers 19 and 20 imbibe and/or absorb and external fluid that enters compartment 14 and form thereby a dispensable composition for transporting ionophores 17 and 18 from dosage form 10. First composition 15 and second composition 16 in a preferred optional embodiment comprise a composition-forming member such as a binder, a tableting agent or a lubricant represented in composition 15 by wavy line 21 and in composition 16 by wavy line 22. Composition-forming members 21 and 22 can be the same or they can be different in compositions 15 and 16.

Dosage form 10 in compartment 14 further comprises an expandable driving member 23 that is in contact with second composition 16. Expandable driving member 23 has a shape that corresponds to the internal shape of compartment 14. Expandable driving member 23, in the presence of an external fluid that enters compartment 14, imbibes and/or absorbs the fluid, increases in size, and thereby pushes against composition 16 to displace first composition 15 and second composition 16 from dosage form 10. Compartment 14 also comprises a dense member or densifier 24 that is in contact with expandable member 23. Dense member 24 is an important component of dosage form 10 for keeping dosage form 10 in the rumen of an animal over a prolonged period of time.

FIG. 4 depicts another manufacture provided by the invention. In FIG. 4, dosage form 10 comprises a body 11 and a wall 12 that surrounds and defines an internal compartment or lumen 14. Wall 12 comprises in a presently preferred embodiment a semipermeable composition that is substantially permeable to the passage of an external fluid and is substantially impermeable to the passage of ingredients contained in dosage form 10. Wall 12 is non-toxic and it keeps its physical and chemical integrity; that is, wall 12 does not erode during the dispensing period. Dosage form 10 also comprises a single composition 15. Composition 15 comprises at least one ionophore 17 homogeneously or heterogeneously dispensed in a pharmaceutically acceptable carrier 19. Carrier 19 is substantially dry during storage of dosage form 10, and when dosage form 10 is in operation in a fluid environment of use and carrier 19 is in contact with the fluid, carrier 19 changes from a rested state to a dispensable state form for delivering ionophore 17 from dosage form 10. Dosage form 10 also comprises a dense member 24 positioned next to a widemouth exit passageway 13 in wall 12. Dense member 24 has a shape that corresponds to the shape of lead end 9 and to the inside shape of dosage form 10. A passageway 25 extends through dense member 24 for delivering beneficial composition 15 comprising ionophore 17 through dense member 24 and then through exit passageway 13 from dosage form 10. Compartment 14 also comprises an expandable member distant from exit passageway 13 at rear end 8. Expandable member 23 is in contact with composition 15 for displacing composition 15 through passageways 25 and 13 from dosage form 10. Composition 15 optionally comprises a composition-forming member 21 such as a binder, a tableting aid or a lubricant for enhancing the manufacture and the displacement of composition 15 from dosage form 10.

FIG. 5 depicts, in opened view, another manufacture provided by the invention. In FIG. 5, dosage form 10 comprises a body 11 and a wall 12 that surrounds and forms internal lumen or compartment 14. Internal compartment 14 comprises composition 15, which composition 15 comprises a pharmaceutically acceptable carrier 19 containing ionophore 17. Compartment 14 also comprises expandable member 23, which member 23 optionally comprises an osmotically effective solute 25. A densifier 24 is present in dosage form 10 positioned distant from lead end 9. Dosage form 10 comprises a multiplicity of exit passageways 13 in wall 12 at lead end 9. Exit passageways 13 comprise a number of multiplicity of smaller openings, generally in a shower-head or screen-like arrangement. The arrangement breaks up composition 15 as composition 15 emerges through the exit passageways 13.

FIG. 6 illustrates another embodiment of dosage form 10 provided by the invention. In FIG. 6, dosage form 10 is seen in opened section and it comprises rear end 8, leading end 9, body 11, wall 12, lumen or compartment 14, first composition 15, second composition 16, ionophore 17, ionophore 18, nontoxic carrier 19, nontoxic carrier 20, composition-forming member 21, composition-forming member 22, expandable member 23, densifier 24, and osmotically effective solute 25. Dosage form 10 comprises a multiplicity of exit openings or passageways 13 that are essentially means for breaking up composition 15 and composition 16 as the compositions are pushed at a controlled rate through the exit openings 13 in wall 12. Exit passageways 13 also function to prevent a premature ejection of a composition from dosage form 10.

FIG. 7 illustrates another embodiment of dosage form 10 provided by the invention. In FIG. 7, dosage form 10 is seen in opened section and it comprises rear end 8, flattened leading end 9, body 11, wall 12, lumen or compartment 14, expandable member 23, densifier 24, and osmotically effective solute 25. In FIG. 7, compartment 14 comprises three ionophore compositions: first composition 15, second composition 16 and third composition 26. First composition 15 includes ionophore 17, nontoxic carrier 19 and composition-forming member 21. Second composition 16 includes ionophore 18, nontoxic carrier 20 and composition-forming member 22. Third composition 26 includes ionophore 27, nontoxic carrier 28 and composition-forming member 29. The three compositions may all comprise the same ionophore or they may comprise different ionophores, the ionophores being present in the same or in differing dosage unit amounts. Dosage form 10 also comprises a multiplicity of exit passageways 13 in wall 12.

The dosage form of the invention can be sized and shaped for delivering an ionophore to a variety of animals. For example, the dosage form can be adapted for delivering an ionophore to ruminant animals including cattle, sheep, giraffes, deer, goats, bison and camels, and more particularly cattle and sheep, that comprise an important group of animals that require periodic administration of an ionophore. Dosage form 10 can embrace a capsule-like shape and in one design have a diameter of from about 0.5 inches to about 1 inch (about 1.3 cm to about 2.5 cm) and a length of from about 0.5 inches to about 2.5 inches (about 1.3 cm to about 6.6 cm). For use with cattle, dosage form 10 has a diameter of from about 0.5 inches to about 1.5 inches (about 1.3 cm to about 3.8 cm), and a length of from about 1 inch to about 4 inches (about 2.5 cm to about 10.2 cm).

While FIGS. 1 through 7 illustrate various dosage forms that can be made according to the invention, it is to be understood that these dosage forms are not to be construed as limiting the invention, as the dosage form can take other shapes, sizes and forms for delivering a beneficial ionophore to the biological environment of use. Additionally, while one, two or three ionophore composition layers are illustrated as presently preferred embodiments, more than three ionophore layers may be present without departing from the invention.

The dosage form of the invention can be used in veterinary clinics, farms, zoos, laboratories, on the range, in feed lots, and in other environments of use.

MODES OF PROVIDING THE INVENTION

In accordance with the practice of this invention, it has now been found that wall 12 can be made with a wall-forming composition that does not adversely affect the animal and does not adversely affect the beneficial ionophore and other ingredients in dosage form 10. Wall 12 in at least part is semipermeable, that is, the wall is permeable to the passage of an external fluid such as water and biological fluids and is substantially impermeable to the passage of ionophore. In a preferred embodiment, all of wall 12 is semipermeable.

Typical materials used for forming wall 12 are, in one embodiment, cellulose esters, cellulose ethers, and cellulose esterethers. The cellulose polymers have a degree of substitution D.S., on their an hydroglucose unit of from greater than 0 up to 3, inclusive. By "degree of substitution" is meant that the average number of hydroxyl groups originally present on the anhydroglucose unit comprising the cellulose polymer that are replaced by a substituting group. Representative materials include a member selected from the group consisting of a cellulose acylate, cellulose diacylate, cellulose triacylate; cellulose acetate, cellulose diacetate, cellulose triacetate; mono-, di-, and tricellulose alkanylates; mono-, di-, and tricellulose aroylates; and the like. Exemplary polymers include cellulsoe acetate having a D.S. up to 1 and an acetyl content up to 21%; cellulose acetate having a D.S. of 1.8 to 2.3 and an acetyl content of 32% to 39%; cellulose diacetate having a D.S. of 1 to 2 and an acetyl content of 21% to 35%; cellulose triacetate having a D.S. of 2 to 3 and an acetyl content of 34% to 44.8%; and the like. More specific cellulose polymers include cellulose propionate having a D.S. of 1.8, a propyl content of 39.2% to 45% and a hydroxyl content of 2.8% to 5.4%; cellulose acetate butyrate having a D.S. of 1.8, an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose triacylate having a D.S. of 2.9 to 3 such as cellulose trivalerate, cellulose trilaurate, cellulose tripalmitate, cellulose trisuccinate and cellulose trioctanoate; cellulose diacylate having a D.S. of 2.2 to 2.6 such as cellulose disuccinate, cellulose dipalmitate, cellulose dioctanoate and cellulose dipentanoate; coesters of cellulose such as cellulose acetate butyrate and cellulose acetate propionate; and the like.

Additional polymers include ethyl cellulose of various degrees of etherification with ethoxy content of from 40% to 55%; cellulose acetate ethyl carbamate; cellulose acetate methyl carbamate cellulose acetate diethyl aminoacetate; semipermeable polyurethanes; semipermeable sulfonate polystyrenes; semipermeable cross-linked polymers formed by the coprecipitation of a polyanion and a polycation as disclosed in U.S. Pat. Nos. 3,173,876, 3,276,586, 3,541,005, 3,541,006, 3,546,142, 4,595,583 and 4,783,337; and the like. Semipermeable polymers also are disclosed by Loeb and Sourirajan in U.S. Pat. No. 3,133,132. Semipermeable lightly cross-linked polymers, semipermeable cross-linked poly(sodium styrene sulfonate), semipermeable cross-linked poly(vinylbenzyltrimethyl) ammonium chloride, semipermeable polymers exhibiting a fluid permeability of $2.5 \times 10^{-8}$ to $2.5 \times 10^{-4}$ ($cm^2/hr.atm$) expressed per atmosphere of hydrostatic or osmotic pressure difference across a semipermeable membrane are disclosed in U.S. Pat. Nos. 3,845,770, 3,916,899 and 4,160,020; and in "Handbook of Common Polymers" by Scott, J. R. and Roff W. J. (1971), published by CRC Press, Cleveland, Oh.

Semipermeable wall 12 also can comprise a flux-regulating agent. The flux-regulating agent is a compound that assists in regulating the permeability of a fluid through the semipermeable wall. Flux-regulating agents that increase the permeability of a wall to fluid, such as water, are essentially hydrophilic. The amount of regulator in the wall, when incorporated therein, generally is from about 0.01 weight percent (wt %) to 35 wt % or more. The flux-regulator agents in one embodiment comprise a member selected from the group consisting of a polyhydric alcohol, polyalkylene glycol, polyalkylenediol, polyester of alkylene glycol, and the like. Typical flux enhancers comprise polyethylene glycol 300, 400, 600, 1500, 4000, 6000, and the like; low molecular weight glycols such as polypropylene glycol, polybutylene glycol, and polyamylene glycol; the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine; 1,2,3-butanetriol, 1,2,4-hexanetriol, 1,3,6-hexanetriol, and the like; esters such as ethylene glycol dipropionate, ethylene glycol butyrate, butylene glycol dipropionate, and the like.

Semipermeable wall 12 optionally comprises a plasticizer, for imparting flexibility and elongation properties to the wall, for making the wall less to nonbrittle, and for enhancing the manufacturing properties of the wall. Plasticizers useful for the present purpose comprise dihexyl phthalate, butyl octyl phthalate, triacetin, dioctyl azelate, epoxidized tallate, sucrose acetate isobutyrate, epoxidized soybean oil, citric acid esters, phosphate esters, tricresyl phosphate, triacetyl phosphate, adipate esters, sebacate esters, and other nontoxic plasticizers. The amount of plasticizer in wall 12, when incorporated therein, is about 0.01 wt % to 40 wt % or more.

Beneficial ionophores that can be dispensed using the dosage form of this invention comprise natural and synthetic ionophores. The ionophores are polyethers and they possess the ability to transport mono- and divalent cations across lipid bilayers which lie within biological membranes. The ionophores possess unique properties which derive from their ability to perturb transmembrane ion gradients and electrical potentials. The ability of ionophores to complex and transport ions leads to their applications as antibiotics against gram-positive microorganisms, against mycobacteria, as growth promotants in ruminants such as cattle and sheep, and for improved feed utilization as seen by increasing the efficiency of meat production. Ionophores that can be stored and dispensed by the dosage form of this invention comprise a member selected from the group consisting of azolomycin, valinomycin, enjactin, monactin, nonactin, dinactin, trinactin, virginiamycin, tetronasin, semduramicin, monensin, monensin sodium, monensin factor B, monensin factor C, nigericin, narasin also known as methyl salinomycin, salinomycin, isolasalocid, lasalocid, lysocellin, septamycin, laidlomycin, laidlomycin propionate, laidlomycin butyrate, lonomycin, lenotemycin, grisorixin, ferensimycin, alborixin, rosgramicin, erythromycin, sodium lysocellin, and the like. The polyethers include bambermycin, monenomycin, flavomycin, and the like. The ionophores also comprise the pharmaceutically acceptable derivative having ionophore activities, such as the pharmaceutically acceptable salts, the alkyl and alkenyl derivatives, the monoglycoside and diglycoside derivatives, the hydroxylated derivatives, the free acid, the hydrate, the ester derivatives, the ether derivatives, and the like. In one presently preferred embodiment, the ionophores exhibit a molecular weight of about 350 to 2500.

The ionophore is present in the invention in a therapeutically effective amount; that is, in an amount that is necessary to provide a desired therapeutic, usually beneficial, effect. The presently preferred amount of an ionophore in a dosage form, present in a single composition, in first and second compositions, or in first, second and third compositions, generally is from about 10 milligrams to 100 grams, preferably from about 10 milligrams to 30 grams. The amount of ionophore in a first and a second composition or in a first, a second and a third composition can be the same or different, with the total amount of ionophore in all compositions in the dispenser equal to a maximum of 100 g, and preferably to a maximum of 30 g. The first, second and/or third compositions can comprise one or more than one like or unlike ionophores. The dosage form provided by the invention can deliver various dosage amounts of an ionophore, for example, from 10 mg per day to 500 mg per day, for 150 days or longer. The ionophores are known in the ionophore art in "Kirk-Othmer Encyclopedia", Vol., 3, pp. 47-64 (1978); Ann. N.Y. Acad. Sci., Vol, 264, pp. 373-86 (1975); and ACS Sym., Ser. 140, pp. 1-22 (1980). The ionophore can be present as a base, as a salt, as an ester, or as another derivative thereof.

The pharmaceutically acceptable carriers 19, 20 and 28 forming the first, second and third compositions 15, 16 and 26 and comprising ionophores 17, 18 and 27 comprise pharmaceutically acceptable polymers that are hydrophilic, nontoxic, and substantially free of reaction with an ionophore and other members forming dosage form 10. The pharmaceutically acceptable carrier comprising an ionophore provides unexpected advantage such as (a) the ability to store a high dosage amount, up to 95 wt %, of an ionophore; (b) the ability to dispense an ionophore in controlled, small doses over a prolonged time up to about 5 or 6 months or longer; (c) the ability to substantially protect a fluid sensitive ionophore from fluid that enters the dosage form, by harboring the ionophore within its polymeric structure; and (d) the ability to charge high loadings of an ionophore in a polymer carrier that undergoes change from a rested state to a dispensable state possessing a dispensable viscosity, or to a semisolid dispensable state during operation of the dosage form. The polymer carriers useful for the present purpose comprise a member selected from the group including polyethylene oxide polymers having a 1,000,000 to 7,500,000 molecular weight; carboxy vinyl polymers, sometimes referred to as carboxymethylene, commercially available as Carbopol ® polymer possessing a 200,000 to 5,000,000 molecular weight; poly(vinyl pyrrolidone) having a 125,000 to 460,000 molecular weight; poly(hydroxyalkyl methacrylate) having a 100,000 to 5,000,000 molecular weight; polysaccharides such as agar, karaya, tragacanth, algin, guar, nanthan, and the like, having a 50,000 to 2,000,000 molecular weight; and the like.

Expandable layer 23, useful for displacing the first composition, the second composition and/or the third composition from the dosage form, comprises a hydrogel composition. The hydrogel composition is non-cross-linked or optionally lightly cross-linked and it possesses osmotic properties such as the ability to imbibe an exterior fluid through the semipermeable wall and exhibit an osmotic pressure gradient across the semipermeable wall. The polymer exhibits the ability to retain a significant fraction of the imbibed fluid in the polymer structure. The polymers in a preferred embodiment are gel polymers that can swell or expand to a very high degree, usually exhibiting a 2- to 50-fold volume increase, thereby pushing and displacing the composition comprising the ionophore from the dosage form. The swellable, hydrophilic polymers also are known as osmopolymers. The polymers can be of plant, animal or synthetic origin. Polymeric materials useful for forming the expandable layer comprise anionic and cationic hydrogels; polyelectrolyte complexes; a mixture of agar and carboxymethylcellulose; a composition comprising methylcellulose mixed with sparingly cross-linked agar; a water-swellable polymer of N-vinyl lactams; polyethylene oxide possessing a 1,000,000 to 10,000,000 molecular weight; starch graft polymers; sodium carboxymethylcellulose having a 90,000 to 1,000,000 molecular weight; a composition comprising sodium carboxymethylcellulose and a member selected from the group consisting of hydroxypropylcellulose and hydroxypropylmethylcellulose; and the like. Representative polymers possessing hydrophilic properties are known in U.S. Pat. Nos. 3,865,108, 4,002,173, 4,207,893 and 4,327,725, and in *Handbook of Common Polymers* by Scott and Roff, published by the Cleveland Rubber Company, Cleveland, Oh.

Expandable polymer layer 23 optionally comprises an osmotically effective compound 25. Osmotically effective compounds also are known as osmotically effective solutes and as osmagents. The osmotically effective compounds exhibit and osmotic pressure gradient across semipermeable wall 12, and they imbibe fluid into compartment 14. The presence of this imbibed fluid provides added fluid for the expandable polymer to absorb and increase its volume, and the imbibed fluid continuously fills the driving area of the compartment and forms a push member that urges the first composition, the second composition and/or the third composition from dosage form 10. Osmotically effective compounds or solutes useful for the present purpose comprise magnesium sulfate, magnesium chloride, sodium chloride, potassium chloride, lithium chloride, potassium sulfate, sodium sulfate, mannitol, urea, sorbitol, inositol, sucrose, glucose, a mixture of sodium chloride and magnesium chloride, a mixture of potassium chloride and sucrose, and the like. The osmotic pressure in atmospheres, atm, of osmotically effective compounds suitable for the invention will be greater than zero atm, generally from eight atm up to 500 atm, or higher. The amount of osmotically effective compound blended homogeneously or heterogeneously with the swellable polymer is from about 0.02 wt % to 50 wt %. Osmotically effective solutes are known in U.S. Pat. Nos. 4,595,583 and in 4,783,337.

Composition-forming members or tableting aids 21, 22 and 29 optionally used to provide compositions 15, 16 and 26 may comprise, for example, binders that impart cohesive qualities to the composition such as poly(vinyl pyrrolidone), natural and synthetic gums such as sodium alginate, methylcellulose, hydroxypropylmethylcellulose, Veegum ®, waxes, and the like; to prevent adhesion to dies and punches during tableting processes, such as a magnesium stearate, calcium stearate, stearic acid, talc, lycopodium, and the like; coloring agents for esthetic qualities and identification such as FD&C Blue No. 1; surfactants that aid in dispensing the ionophore after its release from the dosage form, such as anionic, cationic, nonionic and amphoteric surfactants; and the like. Composition-forming members are disclosed in *Pharmaceutical Sciences*, Remington, 14th Ed. (1970). The amount of composition-forming member present in the composition is from about 0.01 wt % to 20 wt %.

The dense member 24, also referred to as density member or densifier 24, is used in delivery system 10 to retain the dosage form in the rumen-reticular sac of a ruminant. Dense member 24 allows dosage form 10 to remain in the rumen over a prolonged period of time, rather than letting it pass into the alimentary tract and be eliminated therefrom. As dosage form 10 remains in the rumen, beneficial ionophore is delivered at a controlled rate to the ruminant over a prolonged period up to 6 months or longer. Generally, dense member 24 will have a density of from about 1.0 to 8, or higher, with the density in a presently preferred embodiment exhibiting a specific gravity of from 1.5 to 7.6. For the ruminants cattle and sheep, it is presently preferred that dense member 24 exhibit a density to assure complete system density of 2 to 3 or greater. Materials that have a density that can be used for forming dense member 24 include iron, iron oxide, iron shot, iron shot coated with iron oxide, iron shot magnesium alloy, steel, stainless steel, copper oxide, a mixture of copper oxide and iron powder, and the like. Density of the device may also be achieved by incorporation of barium sulfate. Dense member 24 in dosage form 10 can embrace different embodiments. For example, dense member 24 can be machined or cast as a single, solid piece made of stainless steel having a density of 7.6. The solid member is made having a shape that corresponds to the internal shape of system 10. Dense member 24 in another manufacture can be a solid member having an axially aligned bore that extends through the length of the member. In another embodiment, dense member 20 can comprise a plurality of dense pellets.

The expression "exit passageway 13", as used herein, denotes an opening or a means in wall 12 suitable for releasing the composition comprising the ionophore from dosage form 10. The invention provides a passageway for releasing a composition intact and it also provides a passageway means, such as a multiplicity of passageways, for dividing the original composition into smaller compositions as it is released from dosage form 10. The release of a composition from dosage form 10, in either instance, embodies a combination of osmotic hydrodynamic pumping and diffusion properties through an exit passageway or through a series of exit passageways functioning as an exit port. The dosage form provided by this invention maximizes the release by osmotic pumping and minimizes the release by diffusion, thereby substantially avoiding mechanical agitation-dependent drug release. The release rate pattern from a drug dosage form, for example, designed to deliver 85 mg/day of the drug lysocellin is as follows in Equation (1):

$$\left[\frac{dm}{dt}\right]_t = \left[\frac{dm}{dt}\right]_o + \left[\frac{dm}{dt}\right]_d \tag{1}$$

wherein:

$\left[\dfrac{dm}{dt}\right]_t$ is the total amount of drug released from the device per unit time (mg/day);

$\left[\dfrac{dm}{dt}\right]_o$ is the amount of drug released per unit time (mg/day) due to osmotic pumping; and $\left[\dfrac{dm}{dt}\right]_d$ is the amount of drug release per unit time (mg/day) due to diffusion.

Then, assuming that negligible water migrates into the drug composition through the wall, Equation (2) follows:

$$\left[\dfrac{dm}{dt}\right]_o = V \cdot \rho d \cdot L = \left[\dfrac{k}{h}\right] Ap \cdot \Delta\pi \cdot \rho_d \cdot L \quad (2)$$

wherein
V is the release rate from the dosage form at 40° C. in cc/day;
$\rho_d$ is the drug+pharmaceutical carrier density in mg/cc;
L is the percent drug loading;
k is the water permeability of the wall at 40° C. in $$\dfrac{cm^3 \, mil}{cm^2 \, hr \, atm} ;$$

h is the wall thickness in mil (or in mm);
Ap is the surface of the push-composition in contact with the wall; the bottom and top surfaces of the push composition are in contact with the density element and the drug composition respectively; and,
$\Delta\pi$ is the water imbibition pressure atm.

During operation of the dosage form, $Ap \times \Delta\pi$ remains constant; and their operation can be illustrated by the accompanying graph wherein $Ap \times \Delta\pi = C$; and

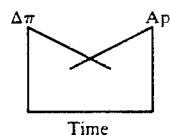

wherein, any decrease in osmotic activity is compensated for by an increase in the area of the push composition in contact with the wall. Therefore, it follows according to Equations (3) and (4):

$$\left[\dfrac{dm}{dt}\right]_o = \left[\dfrac{k}{h}\right] C \cdot \rho_d \cdot L \quad (3)$$

$$\left[\dfrac{dm}{dt}\right]_o = \left[\dfrac{k\pi \times Ap}{h}\right] \rho_d \cdot L \quad (4)$$

The amount of drug delivered due to diffusion into an environment of use initially free of drug is set forth by Equation 5:

$$\left[\dfrac{dm}{dt}\right]_d = \left[\dfrac{d \, Sep \, Cs}{h}\right] L \quad (5)$$

wherein:

$\left[\dfrac{dm}{dt}\right]_d$ is the amount of formulation, comprising lysocellin and pharmaceutical carrier diffusing through the exit port per unit (mg/day);

D is the diffusion coefficient of the formulated drug in rumenal fluid in $cm^2$/day;
Sep is the surface area of the exit port in $cm^2$;
h is the thicknesses of the diffusion layer in cm;
Cs is the solubility of formulated drug in rumenal fluid in mg/ml;
L is the percent drug present in the formulation; and
D/h = K is the dissolution rate constant in cm/day.

The composition the ionophore is intermittently eroded at the exit passageway in the rumen, and the thickness of the diffusion layer varies from zero to several mm in thickness. The diffusion layer at the dosage form environment of use interface is very thin and will having minimal effect on the amount of formulated drug diffusing through the exit passageway into the rumenal fluid. The two major factors which contribute to the diffusion through the exit passageway are:
(1) Surface area of the exit port (Sep); and,
(2) Solubility of the pharmaceutical carrier and the lysocellin ionophore in rumenal fluid (Cs).

Following the above presentation, the osmotic release rate for the dosage form comprising a lysocellin ionophore composition can be calculated to be 67 mg/day. The total release rate (dm/dt)$_t$ for the lysocellin is 85 mg/day. The diffusional release rate for lysocellin is therefore 18 mg/day.

The effect of the exit passageway diameter increase on the lysocellin release rate was calculated to give the following values (for the 85% drug loading):

| (dm/dt)$_t$ mg/day | (dm/dt)$_o$ mg/day | (dm/dt)$_d$ mg/day | Exit passageway diameter mils | Sap exit passageway surface area $cm^2$ |
|---|---|---|---|---|
| 68.7 | 66.7 | 2.04 | 100 | 0.051 |
| 74.8 | 66.7 | 8.13 | 200 | 0.203 |
| 85.0 | 66.7 | 18.31 | 300 | 0.456 |
| 85.0 | 66.7 | 18.31 | 100 × 9* | 0.456 |
| 99.2 | 66.7 | 32.52 | 400 | 0.810 |

*9 passageways of 100 mils each

The diffusional release increases with an increase in the exit diameter. For the 300 mil exit diameter, the diffusional release is 21.5%, but for a 400 ml ext, the diffusional release is 33% of the total lysocellin release rate.

Figure 8:
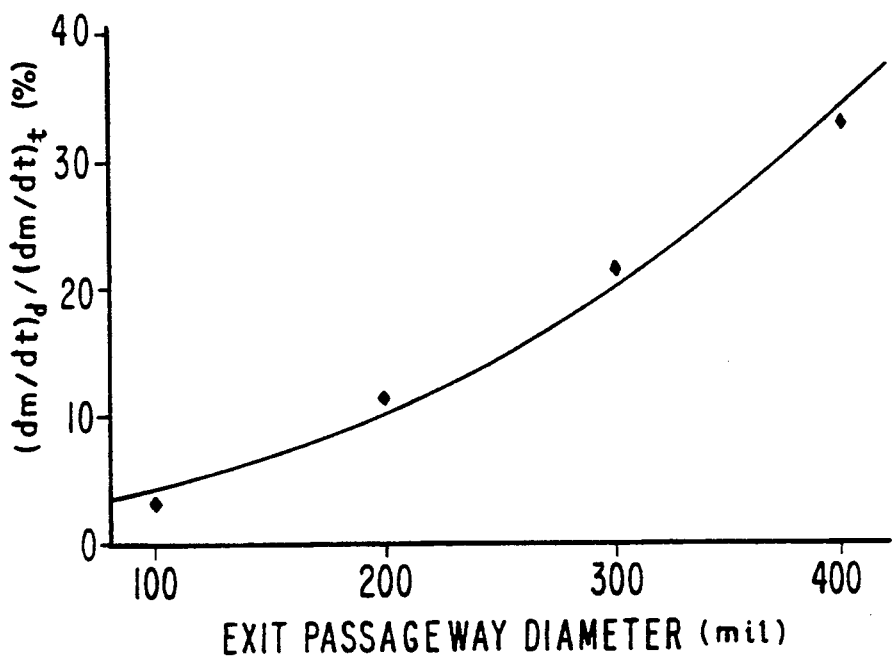
FIGS. 8 through 12 depict release rate patterns for dispensers provided by the invention.

FIG. 8 shows the effects of the exit passageway diameter on the diffusional release of lysocellin. In FIG. 8, one mil equals 0.0254 mm.

Figure 9:
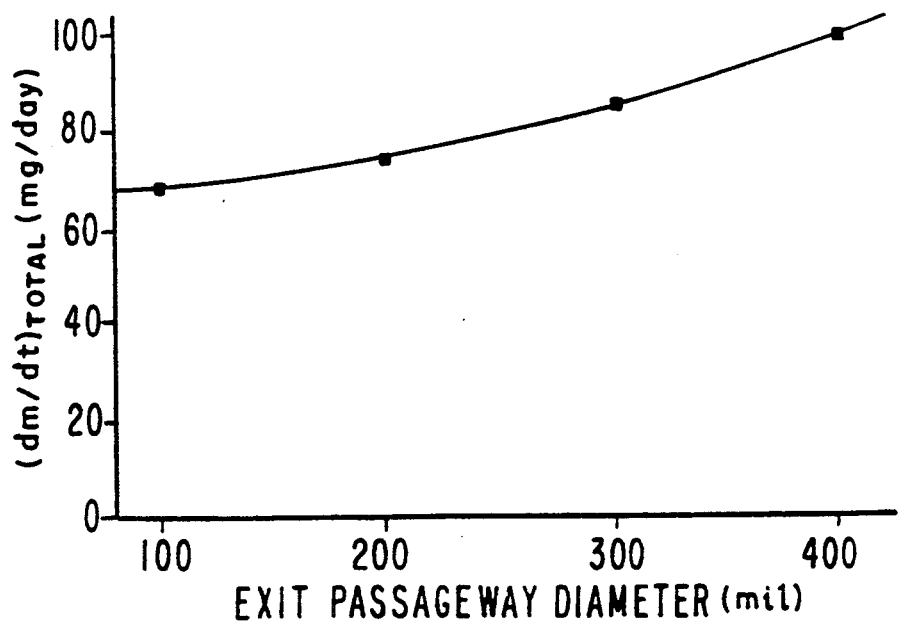

FIG. 9 shows the effects of the exit passageway diameter on the total release of lysocellin from the dosage form.

Figure 10:
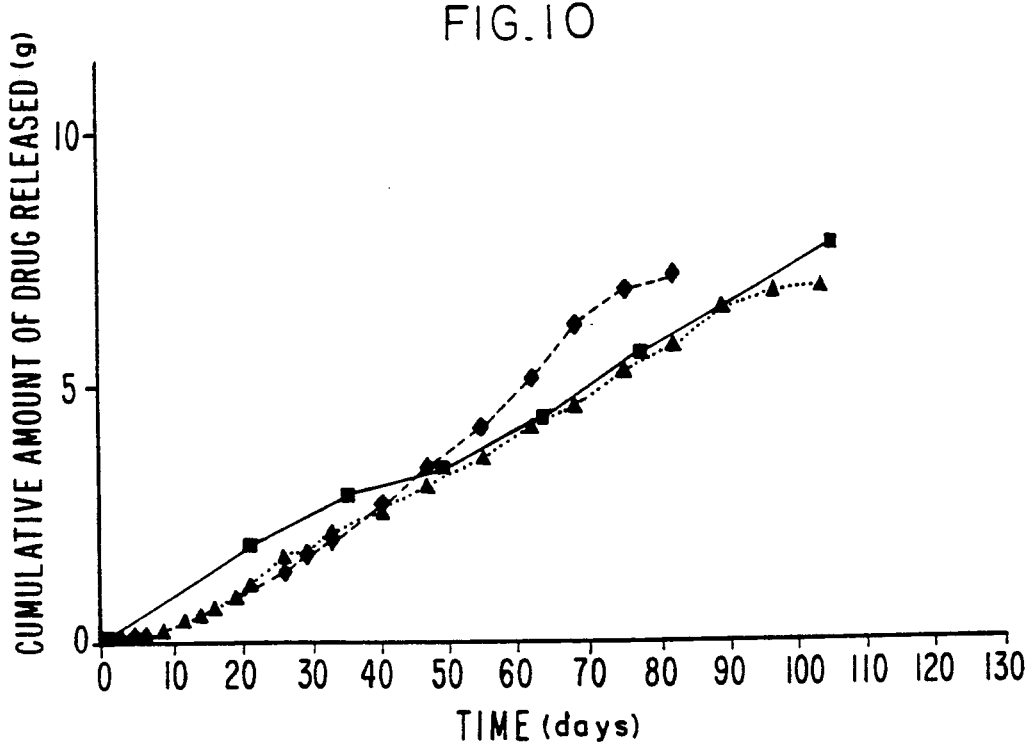
Figure 11:
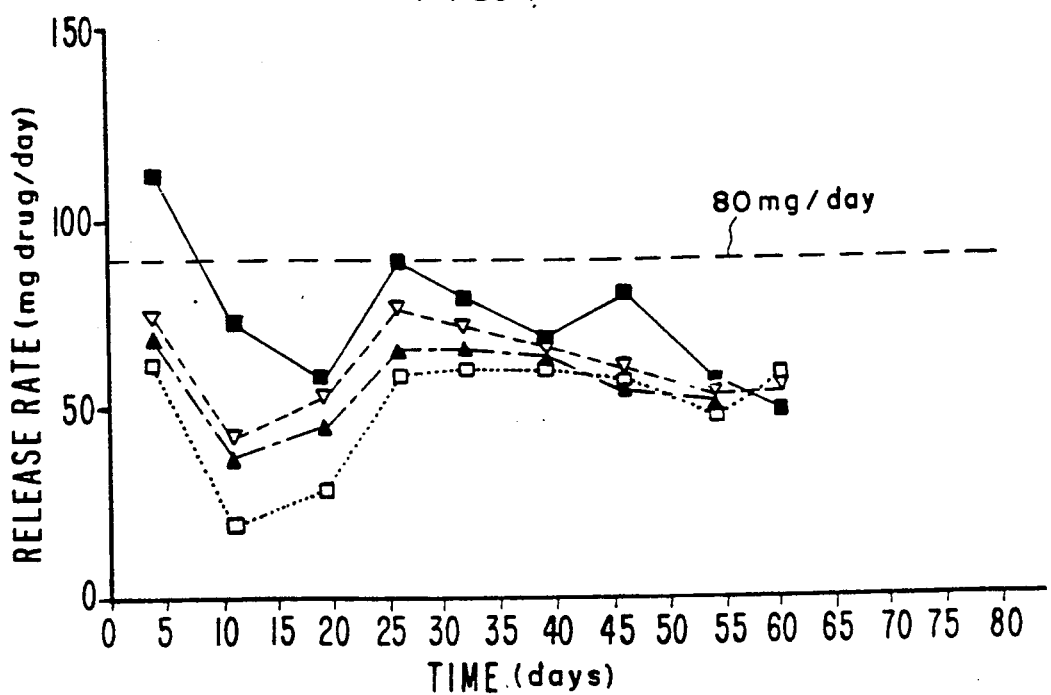

FIG. 10 depicts the functionality of the dosage form. The release rate (dm/dt)$_t$ from the dosage form is about 85 mg/day in vivo. In FIG. 10, the in vivo testing in the rumen of a cow is indicated by squares, the in vitro testing in buffer at pH 8 is indicated by diamonds, and the in vitro testing in artificial rumenal fluid is indicated by triangles. The buffer is a pH 8 buffer consisting of 140.70 g of potassium phosphate and 38.64 g of sodium hydroxide dissolved in 20 liters of distilled water. The artificial rumen fluid consists of 124.69 g of sodium acetate, 53.99 g of sodium propionate, 21.00 g of sodium bicarbonate, 81.02 g of sodium succinate, and 29.92 g of butyric acid dissolved in 20 liters of distilled water, then bubbled with carbon dioxide for 10 minutes.

FIG. 11 shows the results of the effect of the exit diameter increase on the lysocellin release rate. In FIG. 11, the horizontal line connected by dashes indicates a constant release rate of 80 mg/day. The line with squares depicts the release rate through a 400 ml passageway for a composition comprising lysocellin and a hydrophilic polymer having a 7,500,000 molecular weight; the line with triangles pointed up depicts the release rate through a 300 ml passageway by a composition comprising lysocellin and a hydrophilic polymer having a 7,500,000 molecular weight; the line with the triangles pointed down depicts the release rate through a 300 mil passageway for a composition comprising lysocellin and a hydrophilic polymer having a 5,000,000 molecular weight; and, the line with squares depicts the release rate through a 200 mil orifice for a composition comprising a 200 ml passageway and a hydrophilic polymer having a 5,000,000 molecular weight.

The table presented immediately below sets forth the results obtained by comparing the calculated values with the experimental values obtained for a 79% lysocellin loading in a drug composition.

| Drug Carrier Hydrophilic Polymer | Calculated $(dm/dt)_t$ mg/day | Experimental $(dm/dt)_t$ mg/day | Exit Port Diameter mils |
|---|---|---|---|
| 5,000,000 | 79 | 77 | 300 |
| Molecular Weight | 69 | *60 | 200 |
| 7,500,000 | 92 | 90 | 400 |
| Molecular Weight | 79 | *66 | 300 |

The data with an asterisk indicates the experimental value was prepared as follows. The dosage form was designed with one drug composition, comprising 79% or 6 g of lysocellin, and one expandable composition and one composition comprising calcium carbonate. The composition comprising calcium carbonate was used as a filler layer to conserve ionophore. The expandable composition was placed between the ionophore composition and the calcium carbonate composition. The ionophore composition faced the exit port and the calcium carbonate composition faced the density element. Within about three weeks after the experiment began, the expandable composition began to occupy space between the wall and the calcium carbonate composition, thereby diverting some of the push energy away from the exit port and resulting in the indicated values.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the dispensing art in light of the present disclosure, the drawings and the accompanying claims.

EXAMPLE 1

A dosage form manufactured in the shape of a dispenser for the controlled delivery of lysocellin is made as follows. First, 85 g of lysocellin is passed through a 40 mesh screen. Then, 14.75 g of polyethylene oxide having a 5,000,000 molecular weight is passed through a 40 mesh screen. The just-prepared lysocellin and polyethylene oxide are mixed together thoroughly with 0.75 g of hydroxypropylmethylcellulose having a 11,000 molecular weight to provide a homogeneous mix. Then, 30 ml of denatured, anhydrous ethanol is slowly added to the blending mixture, and all the ingredients are mixed for an additional 2 to 3 minutes. The freshly prepared wet granulation is passed through a 20 mesh screen, allowed to dry at room temperature for 16 hours, and again passed through a 20 mesh screen to provide a drug composition.

The drug composition is divided into two portions and compressed to make two different shaped tablets or drug compositions. For one drug tablet, 7.06 g of the drug composition is compressed with a hydraulic press using a flat bottom tablet punch and a deep-concave, top tablet punch. The other tablet is made by compressing 7.06 g of the drug composition using a flat bottom and flat top tablet punch.

Next, an expandable composition is prepared by passing separately through a 40 mesh screen the following ingredients: 84.7 g of sodium carboxymethylcellulose with a 700,000 molecular weight, 9.4 g of hydroxypropylcellulose with a 60,000 molecular weight, 4.7 g of sodium chloride and 1.0 g of ferric oxide. All of the above ingredients are thoroughly mixed to provide a homogeneous mass. Then, with continuous mixing, 40 ml of denatured alcohol is added slowly and the mixing is continued for 2 to 3 minutes. The wet granulation is passed through a 20 mesh screen, dried at room temperature for 16 hours and again passed through a 20 mesh screen. Finally, 0.2 g of magnesium stearate is added to the granulation and the ingredients are mixed in a rollermill for 3 to 4 minutes. The expandable composition is made into a tablet by compressing 5.2 g of the composition in a hydraulic press using a flat top and flat bottom tablet punch.

Next, a wall-forming member designed and shaped like a cup is prepared as follows. First, 76 g of cellulose acetate butyrate having a butyryl content of 37% and 13% acetyl content, 15 g of polyethylene glycol having a 400 molecular weight and 9 g of triethyl citrate are mixed into a homogeneous mass. Then, 10.5 g of the mixture is injection molded to make a semipermeable walled cup with one domed (concave) end and an opposite open end and with an average wall thickness of 65 mils.

The dispenser is assembled as follows. First, a 300 mil exit port is drilled through the concave end of the semipermeable cup. The first described drug tablet is then inserted into the semipermeable cup so that its convex top fits into the concave end of the cup. Then, the second described drug tablet is inserted into the cup so that it is flush against the flat end of the first inserted drug tablet. Next, the expandable tablet is inserted so that it is flush against the second drug tablet. Then, a 64 g iron densifier is inserted into the cup so that its flat end is against the expandable tablet. Finally, the wall is sealed as the open end of the cup is heated, then pressed against the densifier and cooled to room temperature.

Figure 12:
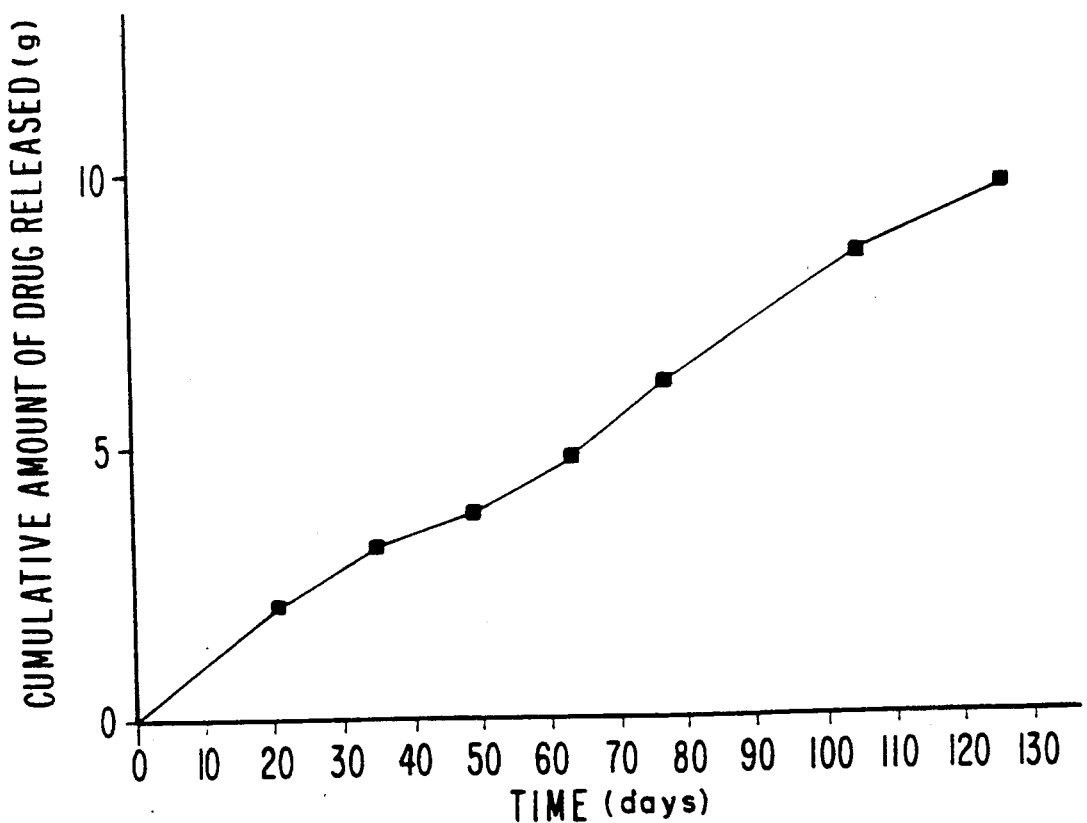
Figure 1:
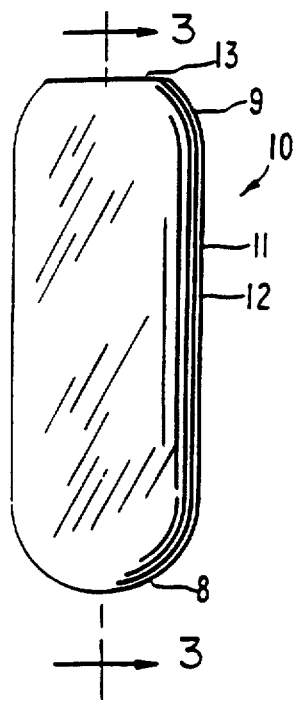
Figure 2:
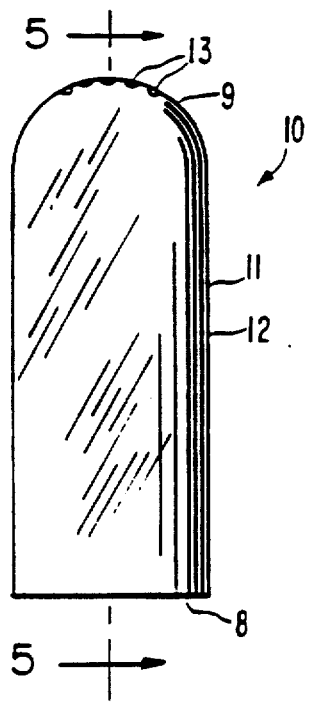
Figure 3:
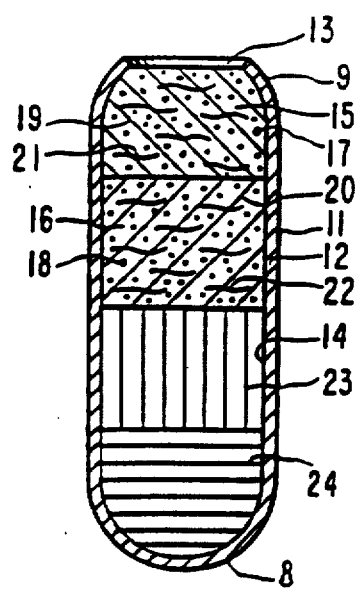

Dispensers prepared according to this example were placed into the rumen of a fistulated cow. The dispensers were removed from the rumen at different time intervals to measure the amount of lysocellin released per unit time. FIG. 12 illustrates the controlled and continuous release of lysocellin at a rate of 85 mg/day for 126 days. In the figure, the squares denote the cumulative amount of lysocellin released (grms.) at different time (days) intervals, and the number of dispensers in the study were seven.

EXAMPLE 2

A dispenser sized and adapted for the controlled delivery of lysocellin is made according to the procedure set forth in Example 1, with all conditions as previously described, except that this example the drug composition comprising the lysocellin is present as a single composition in the dispenser. The single composition weighs 14.12 g and comprises polyethylene oxide having a 5,000,000 molecular weight, hydroxypropylmethylcellulose having a 11,200 molecular weight, and the lysocellin ionophore.

EXAMPLE 3

A dispenser for administering two different carboxylic ionophores, monensin and lasalocid, for increasing feed efficiency in ruminants is manufactured according to the procedure of Example 1. In this example, the dispenser comprises two ionophore compositions, with each composition comprising a different ionophore. A first composition nearest the exit port comprises monensin sodium, polyethylene oxide having a 5,000,000 molecular weight and hydroxypropylmethylcellulose having a 11,200 molecular weight. The second composition is in immediate contact with the first composition. The second composition comprises lasalocid, polyethylene oxide having a 3,000,000 molecular weight and hydroxypropylmethylcellulose having a 22,000 molecular weight. The rest of the dispenser is as described in Example 1. The use of two different ionophores delivered into the rumen operates to maintain maximum feed efficiency. The dispenser can be manufactured for administering the first ionophore composition for 50 to 60 days, followed by delivering the second composition for 50 to 60 days.

EXAMPLE 4

A dispenser for delivering an ionophore to livestock is made by following the above examples. The dispenser of this example is 75 mm long and 25 mm in diameter. The dispenser comprises a pair of compositions in contacting arrangement, with each composition consisting of lasalocid, lysocelline, septamycin, nigericin, dianemycin, monensin and salinomycin; 1,054 mg of polyethylene oxide possessing a 5,000,000 molecular weight; 162.50 mg of hydroxypropylmethylcellulose possessing a 11,200 molecular weight; and 125 mg of magnesium stearate. The dispenser comprises a single expandable composition layer in contact with a pair of ionophore compositions. The expandable composition comprises 4,405 mg of sodium carboxymethylcellulose having a 700,000 molecular weight, 490 mg of hydroxypropylcellulose, 245 mg of sodium chloride, 50 mg of ferric oxide, and 15 mg of magnesium stearate. The device contains a 64,000 mg iron densifier, a 10,500 mg cellulosic rate-controlling wall, and a 400 mil diameter exit orifice or passageway.

EXAMPLE 5

A dispensing device for the controlled delivery of an ionophore into the digestive tract of an animal is manufactured as follows. First, 57 g of cellulose acetate having an acetyl content of 39.8% and 1.3 kg of cellulose acetate butyrate having an acetyl content of 13% and a butyryl content of 37% are sized and then combined with 2.2 g of Citroflex ®-2 triethyl citrate and 0.3 kg of polyethylene glycol 400 in the bowl of a large Hobart ® mixer. After mixing for 20 minutes, the blended material is transferred to the feed hopper of a Van Dorn injection molder, which is equipped with a suitable mold to produce a 7.5 g cellulose cup having the approximate dimensions 6.3 cm in height × 2.1 cm in width and a wall thickness of 0.13 cm.

Next, 4.0 g of a hydrophilic expandable member comprising a 70:30 ratio of sodium carboxymethylcellulose to sodium chloride, lubricated with 1% magnesium stearate, is compressed using 10,000 lbs. of force in a Carver ® laboratory press equipped with a tablet tool and is then inserted into the cup.

Next, an ionophore composition comprising 10 g of an ionophore selected from the group consisting of lonomycin, lentotemycin, etheromycin, isolasalocid, laidlomycin sodium salt, semduramicin, and alborixin potassium salt; 2.1 g of poly(ethylene oxide) having a 3,500,000 molecular weight; 0.325 g of hydroxypropylmethylcellulose having a 11,200 molecular weight; and 0.5 g of magnesium stearate is pressed into a solid tablet and is inserted into the cup against the expandable member.

Then, an iron density element comprising four 50 mm exit passageways, which possesses the dual function of aiding in the retention of the dispenser in the rumen of an animal and serving as a flow moderator through its multiplicity of passageways, is inserted into the open end of the dispenser and seated against the ionophore composition. The protruding lip of the cup is heated until softened using a hot air gun capable of delivering 600° F. air, and the lip is crimped over the perimeter of the density element to provide the dispenser.

EXAMPLE 6

A dispensing device for the delivery of lysocellin to livestock is made following the procedures of the above examples. First, a semipermeable membrane cup having a composition of 79 wt % cellulose acetate butyrate (acetyl content 13% and butyryl content 37%), 15 wt % Citroflex-2 triethyl citrate and 6 wt % poly(ethylene glycol) 400 is injection-molded into a shape having a flattened lead end and an opposite open end. Nine exit passageways (orifice channels) of 60 mil diameter each are molded into the lead end. The cup has dimensions of approximately 8.9 cm length, 2.5 cm width and 0.35 cm wall thickness, with the length (depth) of the passageways being 70 mil.

An ionophore composition comprising 82.0 wt % lysocellin, 16.0 wt % polyethylene oxide, 1.0 wt % hydroxypropylmethylcellulose E-5 and 1.0 wt % magnesium stearate is pressed into three solid tablets, each weighing 5.0 g. One tablet is inserted into the open end of the cup and seated against the lead end, the second tablet is then inserted behind the first, and the third tablet is inserted behind the second.

Next, 9.1 g of a hydrophilic expandable tablet is formed, the tablet having the following composition: 63.0 wt % sodium carboxymethylcellulose, 30.0 wt % sodium chloride, 4.75 wt % hydroxypropylcellulose EF, 1.0 wt % hydroxypropylmethylcellulose E-5, 1.0 wt % ferric oxide, and 0.25 wt % magnesium stearate. The expandable tablet is inserted into the semipermeable membrane cup behind the third ionophore tablet.

A density element having a density of 6.7 g/cc is then placed in the membrane cup behind the expandable tablet. The protruding lip of the cup is heated until softened and the lip is crimped over the perimeter of the density element to provide the dispenser.

EXAMPLE 7

Lysocellin dispensers identical to those prepared in Example 6 are made, except that the lead end is of a domed rather than a flattened shape.

Dispensers were tested in vitro and also in vivo in fistulated cattle. The average release rate was 70–80 mg of lysocelline per day at week 18. Lysocellin was released from the devices for at least one to 150 days.

EXAMPLE 8

Lysocellin dispensers identical to those prepared in Example 6 are made, except that the semipermeable membrane cup is molded so that is has either a) nine exit passageways of 75 mil diameter and 70 mil length each, b) nine exit passageways of 85 mil diameter and 70 mil length each, or c) nine exit passageways of 100 mil diameter and 140 mil length each at its lead end.

EXAMPLE 9

A dispensing device for the delivery of tetronasin to livestock is made following the procedures of the above examples. First, a semipermeable membrane cup having a composition according to Example 6 is molded into a shape having a flattened lead end and an opposite open end. Nine exit passageways of 60 mil diameter each are molded into the lead end.

An ionophore composition comprising 50.0 wt % tetronasin, 21.6 wt % polyethylene oxide coagulent, 26.4 wt % barium sulfate, 1.0 wt % hydroxypropylmethylcellulose E-5 and 1.0 wt % magnesium stearate is pressed into three solid tablets, each weighing 5.0 g. One tablet is inserted into the open end of the cup and seated against the lead end, the second tablet is then inserted behind the first and the third tablet is inserted behind the second.

Next, 9.1 g of a hydrophilic expandable tablet is formed, having the same composition as that in Example 6. The expandable tablet is inserted into the semipermeable membrane cup behind the third ionophore tablet.

A density element having a density of 6.7 g/cc is then placed in the membrane cup behind the expandable tablet. The protruding lip of the cup is heated until softened and the lip is crimped over the perimeter of the density element to provide the dispenser.

EXAMPLE 10

Tetronasin dispensers identical to those prepared in Example 9 are made, except that the lead end is of a domed rather than a flattened shape.

Dispensers were tested in vitro and also in vivo in fistulated cattle. The average release rate was 55–60 mg of tetronasin per day at week 18. Tetronasin was released from the devices for at least up to 150 days.

EXAMPLE 11

Tetronasin dispensers identical to those prepared in Example 9 are made, except that the semipermeable membrane cup is molded so that it has either a) nine exit passageways of 75 mil diameter and 70 mil length each, b) nine exit passageways of 85 mil diameter and 70 mil length each, or c) nine exit passageways of 100 mil diameter and 140 mil length each at is lead end.

METHOD OF USING THE INVENTION

An embodiment of the invention pertains to a method for administering a beneficial ionophore at a controlled rate to the rumen of a ruminant. In carrying out the method, a dispenser is placed into a balling gun provided with an ejecting means, the gun is inserted into the mouth of the animal beyond the base of the tongue, and the dispenser is gently ejected by applying pressure to an ejection plunger in the gun, thereby sending the dispenser into the rumen. More specifically the method comprises the steps of: (A) admitting into an animal's rumen a dispenser comprising: (1) a wall comprising in at least a part a semipermeable polymer composition permeable to the passage of fluid and substantially impermeable to the passage of an ionophore, the wall surrounding (2) an internal lumen or compartment, (3) a layer comprising a beneficial ionophore and a pharmaceutically acceptable carrier for the ionophore in the lumen, (4) a layer of an expandable hydrophilic polymeric composition in the lumen, (5) a dense member in the lumen for maintaining the dispenser in the rumen over a prolonged period of time, and (6) at least one exit passageway in the wall that communicates with the composition comprising the ionophore and the carrier; (B) imbibing fluid through the semipermeable wall at a rate determined by the permeability of the wall and the osmotic pressure gradient across the wall, which fluid contacts the composition comprising the ionophore to form a dispensable composition and contacts the expandable composition to cause the expandable composition to expand and push against the ionophore composition; and (C) delivering the beneficial ionophore composition from the lumen by the expandable composition continually expanding against the ionophore composition and causing the ionophore to be dispensed in a beneficially effective amount through the exit passageway at a controlled rate to the rumen over a prolonged period of time.

Inasmuch as the foregoing specification comprises presently preferred embodiments of the invention, it is to be understood that various improvements and modifications may be made her in accordance with the inventive principles disclosed, without departing from the scope of the invention.

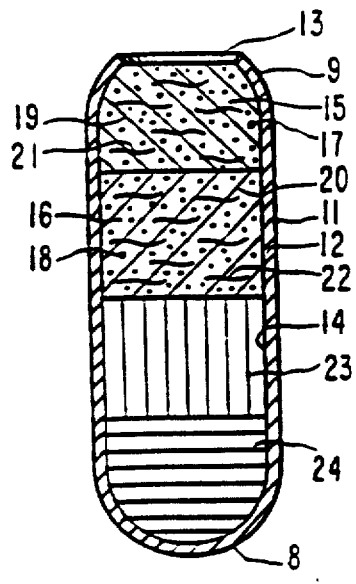

What is claimed is:

1. A dispenser for delivering a beneficial ionophore to a fluid environment of use, the dispenser comprising:
    (a) a wall comprising in at least a part a semipermeable composition permeable to the passage of fluid and substantially impermeable to the passage of an ionophore, which wall surrounds
    (b) a compartment;
    (c) a composition in the compartment comprising an ionophore and a pharmaceutically acceptable carrier for the ionophore;
    (d) a hydrophilic polymeric composition in the compartment that expands in the presence of fluid for pushing the composition comprising the ionophore from the dispenser;

(e) a densifier in the compartment, the densifier having a specific gravity greater than the specific gravity of fluid present in the environment of use; and (f) an exit passageway or multiplicity of exit passageways in the wall for delivering a therapeutically effective amount of the ionophore from the dispenser over a period of time, the diameter of each exit passageway being of a size to maximize release of the ionophore by osmotic pumping and minimum the release of the ionophore by diffusion to avoid mechanical agitation-dependent ionophore release.

2. A dispenser according to claim 1 wherein the ionophore is lysocellin.

3. A dispenser according to claim 1 wherein the ionophore is tetronasin.

4. A dispenser according to claim 1 wherein the ionophore is a member selected from the group consisting of lonomycin, lenotemycin, erythromycin, isolasalocid, laidlomycin, laidlomycin propionate, laidlomycin butyrate, semduramicin, alborixin, lasalocid, septamycin, nigericin, dianemycin, monensin, and salinomycin, and pharmaceutically acceptable salts and esters thereof.

5. A dispenser according to claim 1 wherein the dispenser delivers the ionophore for about 150 days.

6. A dispenser for delivering a beneficial ionophore to a fluid environment of use, the dispenser comprising:

(a) a wall comprising in at least a part a nontoxic composition permeable to the passage of fluid and substantially impermeable to the passage of an ionophore, the wall surrounding and forming (b) a compartment;

(c) a composition in the compartment comprising an ionophore and a pharmaceutically acceptable carrier for the ionophore;

(d) a second composition in the compartment comprising an ionophore and a pharmaceutically acceptable carrier for the ionophore;

(e) a hydrophilic polymeric composition in the compartment comprising an osmotic composition that expands when contacted by fluid to displace the first and second compositions from the dispenser;

(f) a densifier in the compartment, the densifier having a specific gravity greater than the specific gravity of fluid present in the environment of use; and (g) an exit passageway or multiplicity of exit passageways in the wall for delivering the first and second compositions from the dispenser in therapeutically effective amounts over a period of time, the diameter of each exit passageway being of a size to maximize release of the ionophore by osmotic pumping and minimum the release of the ionophore by diffusion to avoid mechanical agitation-dependent ionophore release.

7. A dispenser according to claim 6 wherein the ionophore in the first composition is lysocellin or tetronasin.

8. A dispenser according to claim 6 wherein the ionophore in the second composition is lysocellin or tetronasin.

9. A dispenser according to claim 6 wherein the first composition and the second composition comprise the same ionophore.

10. A dispenser according to claim 9 wherein the ionophore is lysocellin or tetronasin.

11. A dispenser according to claim 6 wherein the first composition and the second composition comprise different ionophores.

12. A dispenser according to claim 6 wherein the dispenser delivers an ionophore for about 150 days.

13. A dispenser according to claim 6 wherein the ionophore in the first composition comprises an ionophore selected from the group consisting of valinomycin, enniactin, monactin, nonactin, dinactin, trinactin, virginiamycin, tetronasin, semduramicin, monensin, monensin sodium, nigericin, narasin, salinomycin, isolasalocid, lasalocid, lysocellin, septamycin, laidlomycin, laidlomycin propionate, laidlomycin butyrate, lonomycin, lenotemycin, grisorixin, alborixin, erythromycin, azolomycin, and sodium lysocellin, and pharmaceutically acceptable salts and esters thereof.

14. A dispenser according to claim 6 wherein the ionophore in the second composition comprises a member selected from the group consisting of valinomycin, enniactin, monactin, nonactin, dinactin, trinactin, virginiamycin, tetronasin, semduramicin, monensin, monensin sodium, nigericin, narasin, salinomycin, isolasalocid, lasalocid, lysocellin, septamycin, laidlomycin, laidlomycin propionate, laidlomycin butyrate, lonomycin, lenotemycin, grisorixin, alborixin, erythromycin, azolomycin, and sodium lysocellin, and pharmaceutically acceptable salts and esters thereof.

15. A dispenser according to claim 6 which further comprises a third composition in the compartment comprising an ionophore and a pharmaceutically acceptable carrier for the ionophore.

16. A dispenser according to claim 15 wherein the ionophore in the third composition comprises a member selected from the group consisting of valinomycin, enniactin, monactin, nonactin, dinactin, trinactin, virginiamycin, tetronasin, semduramicin, monensin, monensin sodium, nigericin, narasin, salinomycin, isolasalocid, lasalocid, lysocellin, septamycin, laidlomycin, laidlomycin propionate, laidlomycin butyrate, lonomycin, lenotemycin, grisorixin, alborixin, erythromycin, azolomycin, and sodium lysocellin, and pharmaceutically acceptable salts and esters thereof.

17. A composition for dispensing an ionophore from a drug delivery dispenser to livestock over a prolonged period of time, said composition comprising 10 mg to 100 g of an ionophore selected from the group consisting of valinomycin, enniactin, monactin, nonactin, dinactin, trinactin, virginiamycin, tetronasin, semduramicin, monensin, monensin sodium, nigericin, narasin, salinomycin, isolasalocid, lasalocid, lysocellin, septamycin, laidlomycin, laidlomycin propionate, laidlomycin butyrate, lonomycin, lenotemycin, grisorixin, alborixin, erythromycin, azolomycin, and sodium lysocellin, and pharmaceutically acceptable salts and esters thereof; and a pharmaceutically acceptable poly(ethylene oxide) carrier comprising a 200,000 to 7,500,000 molecular weight.

18. A composition according to claim 17 wherein the ionophore is lysocellin, laidlomycin propionate or tetronasin.

19. A method for administering to an animal a biologically active ionophore, said method comprising:

(A) admitting orally into the animal a dispenser comprising:

(1) a wall that surrounds and forms an internal compartment, the wall comprising in at least a part a composition permeable to the passage of fluid and substantially impermeable to the passage of an ionophore;
(2) a composition in the compartment comprising a biologically active ionophore selected from the group consisting of valinomycin, enniactin, monactin, nonactin, dinactin, trinactin, virginiamycin, tetronasin, semduramicin, monensin, monensin sodium, nigericin, narasin, salinomycin, isolasalocid, lasalocid, lysocellin, septamycin, laidlomycin, laidlomycin propionate, laidlomycin butyrate, lonomycin, lenotemycin, grisorixin, alborixin, erythromycin, azolomycin, and sodium lysocellin, and pharmaceutically acceptable salts and esters thereof; and a pharmaceutically acceptable carrier for the ionophore, said carrier comprising a poly(ethylene oxide) comprising up to 90 wt % of the ionophore;
(3) a hydrophilic composition in the compartment that expands when contacted by fluid, thereby exerting pressure against the ionophore composition for displacement of the ionophore composition from the compartment;
(4) a densifier in the compartment for maintaining the dispenser in the animal over time, the densifier having a density greater than the density of the fluid present in the animal; and
(5) an exit passageway or multiplicity of exit passageways in the wall for delivering the biologically active ionophore from the dispenser, the diameter of each exit passageway being of a size to maximize release of the ionophore by osmotic pumping and minimum the release of the ionophore by diffusion to avoid mechanical agitation-dependent ionophore release; and
(B) administering the biologically active ionophore by the ionophore composition absorbing fluid to form a dispensable composition and by the hydrophilic composition absorbing fluid, expanding and displacing the ionophore composition through the passageway or passageways in a therapeutically effective amount to the animal at a controlled rate over time.

20. A method according to claim 19 wherein the ionophore is lysocellin, laidlomycin propionate or tetronasin.

21. A dispenser according to claim 4 wherein the ionophore is laidlomycin propionate.

22. A dispenser according to claim 9 wherein the ionophore is laidlomycin propionate.

* * * * *

UNITED STATES PATENT AND TRADEMARK OFFICE
CERTIFICATE OF CORRECTION

PATENT NO. : 5,126,142

DATED : June 30, 1992

INVENTOR(S) : Atul D. Ayer; Terry L. Burkoth; Anthony L. Kuczynski and Joseph C. Deters It is certified that error appears in the above-identified patent and that said Letters Patent is hereby corrected as shown below:

In claim 1, at column 19, bridging lines 11-12, delete "minimum" and insert in lieu thereof --minimize--.

In claim 6, at column 19, line 56, delete "minimum and insert in lieu thereof --minimize--.

In claim 19, at column 22, line 8, delete "minimum" and insert in lieu thereof --minimize--.

Delete drawing Sheet 1 of 5 showing FIG. 3 with the dense member numbered "28" and replace with new Sheet 1 of 5 (attached) showing FIG. 3 with the dense member numbered --24--.

The title page should be deleted to appear as per attached title page.

Signed and Sealed this

Twenty-fourth Day of August, 1993

Attest:

BRUCE LEHMAN

Attesting Officer     Commissioner of Patents and Trademarks

United States Patent [19]

Ayer et al.

[11] Patent Number: 5,126,142
[45] Date of Patent: Jun. 30, 1992

[54] DISPENSER COMPRISING IONOPHORE

[75] Inventors: Atul D. Ayer; Terry L. Burkoth; Anthony L. Kuczynski, all of Palo Alto; Joseph C. Deters, Los Altos, all of Calif.

[73] Assignee: ALZA Corporation, Palo Alto, Calif.

[21] Appl. No.: 641,023

[22] Filed: Jan. 11, 1991

Related U.S. Application Data

[63] Continuation-in-part of Ser. No. 381,423, Jul. 18, 1989.

[51] Int. Cl.⁵ ................................................ A23K 1/18
[52] U.S. Cl. ........................................ 424/438; 424/473; 424/422
[58] Field of Search .................... 424/438, 473, 422

[56] References Cited

U.S. PATENT DOCUMENTS

| | | | |
|---|---|---|---|
| 3,133,132 | 5/1965 | Loeb et al. | 264/49 |
| 3,173,876 | 8/1965 | Zobrist | 252/137 |
| 3,276,586 | 10/1966 | Rosaen | 210/90 |
| 3,541,005 | 11/1970 | Strathmann et al. | 210/19 |
| 3,541,006 | 11/1970 | Bixler et al. | 210/23 |
| 3,546,142 | 12/1970 | Michaels et al. | 260/2.1 |
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 4,002,173 | 1/1977 | Manning et al. | 128/296 |
| 4,160,020 | 7/1979 | Ayer et al. | 424/15 |
| 4,207,893 | 6/1980 | Michaels | 128/260 |
| 4,327,725 | 5/1982 | Cortose et al. | 421/473 |
| 4,594,483 | 6/1986 | Eckenhoff et al. | 424/15 |
| 4,783,337 | 11/1988 | Wong et al. | 424/468 |
| 4,814,181 | 3/1989 | Jordan et al. | 424/472 X |
| 4,871,544 | 10/1989 | Eckenhoff | 424/438 |

OTHER PUBLICATIONS

Ann. N. Y. Acad. Sci. vol. 264, pp. 273-286 (1975).
Feedstuff, pp. 14, 15 and 22 (1989).
Kirk-Othmer Encyclopedia, vol. 3, pp. 47-64, (1978).

Primary Examiner—Thurman K. Page
Assistant Examiner—Leon R. Horne
Attorney, Agent, or Firm—Jacqueline S. Larson; Edward L. Mandell; Paul L. Sabatine

[57] ABSTRACT

A dispenser is disclosed for delivering a beneficial ionophore to an animal. The dispenser comprises (1) a semipermeable housing defining an internal space, (2) at least one composition comprising an ionophore and a pharmaceutically acceptable carrier in the space, (3) an expandable hydrophilic composition in the space, (4) a dense member in the space, and (5) at least one exit passageway in the housing for delivering the ionophore from the dispenser.

22 Claims, 5 Drawing Sheets